United States Patent [19]

Hansen et al.

[11] Patent Number: 5,631,392

[45] Date of Patent: May 20, 1997

[54] HYDROFORMYLATION PROCESS AND BIDENTATE PHOSPHITE LIGAND CATALYSTS USED THEREIN

[75] Inventors: Carolina B. Hansen, Sittard; Antonius J. J. M. Teunissen, Geleen, both of Netherlands

[73] Assignees: DSM N.V., Heerlen, Netherlands; E.I. Du Pont de Nemours and Company, Wilmington, Del.

[21] Appl. No.: 559,807

[22] Filed: Nov. 17, 1995

[30] Foreign Application Priority Data

Nov. 17, 1994 [EP] European Pat. Off. ............ 94203345

[51] Int. Cl.$^6$ ................................ C07F 9/02; C07F 17/02
[52] U.S. Cl. ...................... 556/13; 556/18; 556/136; 558/78; 558/96; 558/117; 558/160; 558/156
[58] Field of Search ................... 556/13, 18, 136; 558/78, 96, 117, 160, 156

[56] References Cited

U.S. PATENT DOCUMENTS

| | | | |
|---|---|---|---|
| 4,612,402 | 9/1986 | Muccigrosso et al. | 568/408 |
| 5,103,035 | 4/1992 | Elnagar et al. | 558/96 |
| 5,210,243 | 5/1993 | Kolich et al. | 556/118 |
| 5,235,113 | 8/1993 | Sato et al. | 568/454 |
| 5,391,801 | 2/1995 | Sato et al. | 558/156 |

FOREIGN PATENT DOCUMENTS

518241A2  12/1992  European Pat. Off. .
518241A3  12/1992  European Pat. Off. .

OTHER PUBLICATIONS

Derwent Abstracts: 009289740 (WPI Acc. No.: 92–417149/51), 007345721 (WPI Acc. No.: 87–342727/49), 003981774 (WPI Acc. No.: 84–127318/20), 003949172 (WPI Acc. No.: 84–094716/15). (1995).

*Primary Examiner*—Johann Richter
*Assistant Examiner*—Jane C. Oswecki
*Attorney, Agent, or Firm*—Cushman Darby & Cushman IP Group of Pillsbury Madison & Sutro, LLP

[57] ABSTRACT

The invention relates to a process for preparing an aldehyde compound by hydroformylation of an ethylenically unsaturated organic compound, using a catalyst system which includes a Group VIII metal and a novel bidentate phosphite ligand. The bidentate phosphite ligand has a chemical structure according to formula (1),

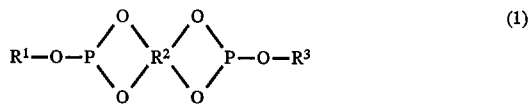

wherein $R^1$ and $R^3$ are respectively substituted or unsubstituted organic groups which may be the same or different, and wherein $R^2$ is a substituted or unsubstituted tetravalent organic group.

12 Claims, No Drawings

HYDROFORMYLATION PROCESS AND BIDENTATE PHOSPHITE LIGAND CATALYSTS USED THEREIN

BACKGROUND OF THE INVENTION

1. Field of the Invention

The invention relates to a novel process for preparing an aldehyde compound via hydroformylation of an ethylenically unsaturated organic compound. The process is catalyzed using a unique bidentate phosphite ligand along with a Group VIII metal, such as rhodium.

2. Background Information

Hydroformylation is a known process by which an ethylenically unsaturated organic compound (such as an olefinic compound and organic compounds carrying functional groups) is converted to an aldehyde containing one carbon more than the starting ethylenically unsaturated organic compound. Specifically, the ethylenically unsaturated organic compound is reacted with hydrogen and carbon monoxide in the presence of a hydroformylation catalyst. The economics of this process require a coordination of maximizing conversion and selectivity at minimum operation cost and low catalyst cost.

There still remains a need for an improved hydroformylation process that is highly efficient and cost-effective, and which maximizes selectivity of the desired product. U.S. Pat. No. 5,235,113 (and related European Patent Application 518,241 and U.S. Pat. Nos. 5,391,801) describe a hydroformylation process using as a catalyst rhodium and a bidentate phosphite ligand. The hydroformylation of 1-octene, toluene, mixed octene, 1-butene, and 1-tetradene is described. The entire contents of EP-A-518,241 and of U.S. Pat. Nos. 5,391,801 and 5,235,113 are incorporated herein by reference.

The ligands in U.S. Pat. No. 5,235,113 are described according to the following general formula:

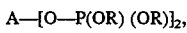

wherein A represents a divalent organic group and R represents an organic group. Unfortunately, the practice of this process still exhibits the unresolved problem that a significant amount of the original olefinic compound is hydrogenated to form an unwanted by-product. This is a serious inefficiency in the process described by U.S. Pat. No. 5,235,113.

SUMMARY OF THE INVENTION

There are four general embodiments of this invention: (1) a novel bidentate phosphite ligand, which is capable of forming a chelate-type bond to a Group VIII metal atom, (2) a novel catalyst system including the novel bidentate phosphite ligand or other ligands, (3) an improved hydroformylation process which uses the novel bidentate phosphite ligand or other ligands, and (4) a process for preparing the novel bidentate phosphite ligand. These embodiments will be discussed in detail below.

To address the above-described inefficiencies in known hydroformylation processes, one object of the present invention is to provide an improved hydroformylation process having a higher selectivity for the conversion of the ethylenically unsaturated organic starting material to the aldehyde product with a diminished degree of hydrogenation of the ethylenically unsaturated organic material to alkanes than has been obtained from processes described in the prior art, and particularly, U.S. Pat. No. 5,235,113.

This object of the invention is achieved by use of a novel hydroformylation process. In this process, an aldehyde compound is prepared by reacting an ethylenically unsaturated organic compound with hydrogen and carbon monoxide under suitable conditions in the presence of a Group VIII metal catalyst and a bidentate phosphite ligand. The bidentate phosphite ligand has a chemical structure according to formula (1):

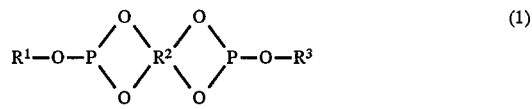

wherein $R^1$ and $R^3$ are substituted or unsubstituted organic groups which may be the same or different, and wherein $R^2$ is a substituted or unsubstituted tetravalent organic group. Preferably, the Group VIII metal catalyst is rhodium.

Preferably, the structure of R2 is sufficiently flexible such that both phosphorous atoms of the bidentate phosphite ligand can bond a single atom of the Group VIII metal catalyst. This is advantageous in that a further improvement of the selectivity towards the aldehyde products and a lower rate of hydrogenation is achieved, especially when starting from internally unsaturated organic compounds.

In a further embodiment, the invention provides a catalyst system consisting essentially of the combination of a Group VIII metal and a bidentate phosphite ligand having a chemical structure according to one of the formulas described herein. The catalyst system may be used in a variety of reactions, including hydroformylation.

In yet a further embodiment, the invention provides certain novel bidentate phosphite ligands having a chemical structure according to any of the above-described formulas, wherein $R^1$, $R^2$ and $R^3$ are the same as defined above, and wherein $R^2$ has a sufficiently flexible structure such that both phosphorous atoms of the bidentate phosphite ligand can bond to one atom of a Group VIII metal.

In another embodiment, the invention provides a process for preparing a bidentate phosphite ligand having a chemical structure according to formula (1) above, wherein $R^1$, $R^2$ and $R^3$ are the same as defined above, and wherein the structure of $R^2$ is sufficiently flexible such that both phosphorous atoms of the bidentate phosphite ligand can coordinate to one atom of a Group VIII metal catalyst. The process comprises the steps of:

(i) reacting a $R^2(OH)_4$ with a phosphoroushalogenide to obtain organic phosphorhalogenide;

(ii) reacting the organic phosphorhalogenide obtained in step (i) with $R^1(OH)$ or $R^3(OH)$ to obtain the desired bidentate phosphite ligand.

Further objects and advantages of the invention will be apparent from the detailed description that follows.

DETAILED DESCRIPTION OF THE INVENTION

The inventors have found that the hydroformylation process of this invention exhibits superior selectivity to aldehyde production and with lessened hydrogenation of the unsaturated starting compound than do the processes described in the art.

An important aspect of this invention contributing to its advantages over the art is the bidentate phosphite ligand having the structural formula (1):

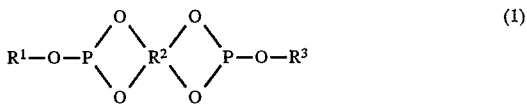

(1)

wherein $R^1$ and $R^3$ are substituted or unsubstituted organic groups which may be the same or different, and wherein $R^2$ is a substituted or unsubstituted tetravalent organic group. Any bidentate phosphite ligand complying with this formula and having the capability of catalyzing hydroformylation reaction in the presence of a Group VIII metal is contemplated by the invention.

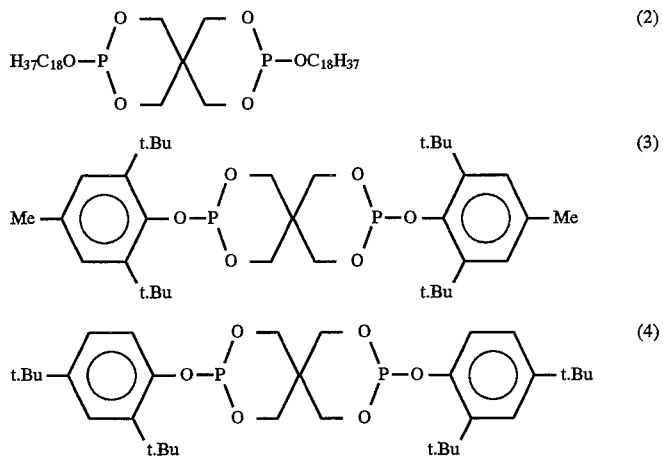

U.S. Pat. No. 5,103,035 describes examples of bidentate phosphite ligands useful in the hydroformylation process of the invention. The contents of U.S. Pat. No. 5,103,035 are entirely incorporated herein by reference.

In the '035 patent, $R^1$ and $R^3$ are alkyl-substituted phenyl groups and $R^2$ is a tetramethylmethane group. However, unlike the present invention, U.S. Pat. No. 5,103,035 only teaches use of these phosphite compounds as stabilizers for polymer compositions.

In the general bidentate phosphite ligand formula (1) of the invention, $R^1$ and $R^3$ preferably have 1 to 30 carbon atoms, and are alkyl, cycloalkyl, aryl, aralkyl or alkaryl groups. Examples of groups for $R^1$ and $R^3$ include the tert-butyl, isopropyl, cyclopentyl, cyclohexyl, phenyl, naphthyl, benzyl, phenethyl, mesityl, tolyl and xylyl groups. Even more preferably, $R^1$ and $R^3$ are aryl, alkaryl or aralkyl groups (such as, for example, phenyl, benzyl or naphtyl groups). $R^1$ and $R^3$ may contain a heteroatom, for example, N, S or Sn.

$R^1$ and $R^3$ can carry one or more organic or inorganic group substituents. For instance, $R^1$ and $R^3$ may carry a $C_{1-12}$ organic group substituent such as, for example, alkyl, aryl, alkoxy and trimethylsilyl groups. Similarly, $R^1$ and $R^3$ may carry inorganic halogen group substituents such as, for example, fluoride, chloride or bromide groups. Preferably, when $R^1$ and/or $R^3$ are aryl or aralkyl groups, $R^1$ and/or $R^3$ are ortho substituted, and the ortho substituents are preferably made with one or more of tert-butyl, tert-propyl, tert-amyl or trimethylsilyl substituents.

In formula (1), $R^2$ is a tetravalent organic group having at least 4 carbon atoms, and preferably, less than 35 carbon atoms.

Examples of bidentate phosphite ligands useful in the catalyst system of the invention include the bidentate phosphite compounds described in U.S. Pat. No. 5,103,035.

Other useful bidentate phosphite ligands include the following ligands of formulas (2), (3) and (4).

In formula (2), $C_{18}H_{37}$ is a linear alkyl group. In formula (3), Me represents a methyl group. In formulas (3) and (4), t.Bu represents a tert-butyl group.

In a preferred embodiment of the invention, the structure of $R^2$ facilitates formation of a chelate complex of the ligand and a Group VIII metal atom. In the context of this invention, the term "chelate complex" means that the Group VIII metal atom/ion is essentially coordinately bound to the two phosphorous atoms of the bidentate fashion ligand. Whether a chelate complex may be formed depends on the particular bridging group of the ligand, that is, the $R^2$ group. Ligands having a flexible $R^2$ group will tend to form a chelate complex with the metal atom/ion. That is, the bridging group $R^2$ between the two phosphorous atoms must be sufficiently flexible so that two phosphorous atoms can coordinate with one metal atom. It has been found that when the structure of $R^2$ is flexible in this manner a further improvement of the selectivity of the hydroformylation reaction to form aldehydes is achieved, especially when starting from terminally unsaturated organic compounds.

Conversely, a "non-chelate complex" means that only one phosphorus atom of the ligand molecule forms a coordinated bond with one Group VIII metal atom or ion in a monodentate fashion.

The ligands according to formula (2), (3) and (4) and the compounds disclosed in U.S. Pat. No. 5,103,035 do not possess a $R^2$ bridging group that is sufficiently flexible to facilitate formation of a chelate complex.

A number of known techniques are available for determining whether a ligand is coordinated to a metal in a monodentate fashion or in a bidentate fashion. For instance, one skilled in the art can employ X-ray crystallography on crystals of the metal complex, or NMR techniques such as $^{31}P$, $^{13}C$ and $^{103}Rh$ NMR. NMR techniques are described in chapter 10 of "The organometallic chemistry of the transition metals" by R. H. Cabtree, John Wiley & Sons, New York, (1994), the entire contents of which are incorporated herein by reference.

Preferably, the flexible bridging groups $R^2$ are tetravalent aryl or alkyl organic groups having at least 8 carbon atoms. Heteroatoms, for example N, S and O, may be present in the $R^2$ group. Examples of flexible $R^2$ bridging groups include
orthoarylene-$(Q)_n$-orthoarylene groups,
alkylene-$(Q)_n$-alkylene groups,
orthoarylene-$(Q)_n$-alkylene groups, and
alkatetrayl groups,
in which n=1, 2, 3 or 4 and Q is —O— (n=1), an aryl group or a —$(CR^4R^5)$— group, in which $R^4$ and $R^5$ individually represent hydrogen or a $C_{1-12}$ alkyl group.

The orthoarylene and alkylene groups may carry one or more substituents of $C_{1-12}$ alkyl groups, as well as phenyl, tolyl, anisyl, and halogen groups (for example, fluoride, chloride and bromide).

Preferably, the orthoarylene group is an orthophenylene group.

Examples of useful alkylene groups include 1,3-isopropanediyl.

Examples of useful orthoarylene groups include orthophenylene (formula (5)) and orthonaphthylene in which the $(Q)_n$ group can be bound to the benzene ring at the numbered positions (formulas (6) and (7)), as shown below.

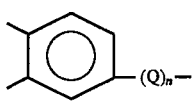
(5)

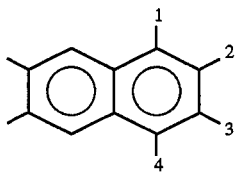
(6)

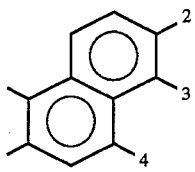
(7)

The alkatetrayl group preferably contains 8 to 15 carbon atoms. For example, the alkatetrayl group may be represented by the following formula (8):

(8)

in which $R^6$ represents a divalent alkylene having at least 2 carbon atoms, and preferably having 2 to 7 carbon atoms. Examples of useful divalent alkylenes include ethylene, trimethylene, diethylene-ether, tetramethylene, pentamethylene and hexamethylene.

The following formulas (9), (10), (11) and (12), are examples of bidentate phosphite ligands having flexible bridging groups $R^2$.

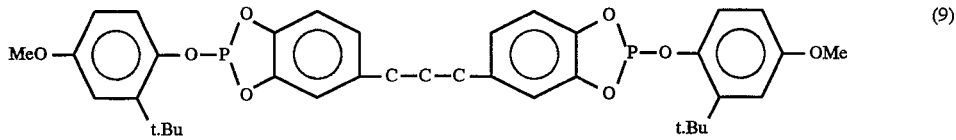
(9)

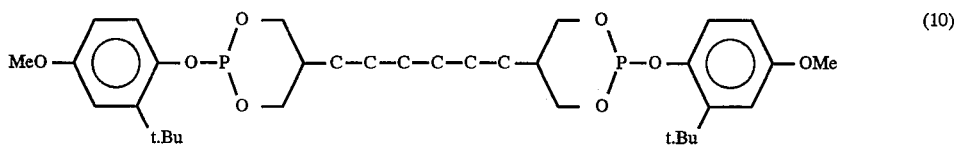
(10)

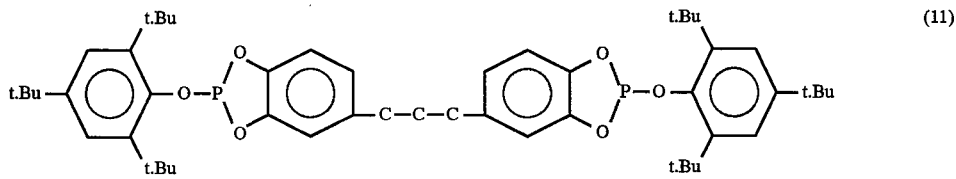
(11)

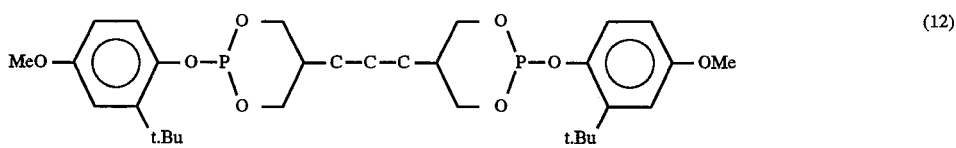
(12)

In the above formulas (9), (10), (11) and (12), MeO is a methoxy group and the —C—C—C— ... groups represent saturated divalent alkyl groups.

Bidentate phosphite ligands according to formula (1) can be prepared according to the techniques described in U.S. Pat. No. 5,103,035.

However, the subject invention also provides novel methods by which bidentate phosphite ligands according to formula (1) can be prepared. In particular, the starting materials include (a) a $R^2(OH)_4$, (b) a phosphorous compound (preferably a phosphorous halogenide (for example, $PCl_3$)) and (c) $R^1(OH)$ or $R^3(OH)$.

Preferably the bidentate ligand is made by first reacting the phosphorous compound with the $R^2(OH)_4$ to form an alkyl or aryl phosphorchloride. The alkyl or aryl phosphorchloride is then further reacted with $R^1(OH)$ or $R^3(OH)$ in order to obtain the desired ligand product. If necessary or desired, the bidentate phosphite ligand can be purified by crystallization or column chromatography.

Another embodiment of the invention entails a novel catalyst system consisting essentially of the combination of the above-described bidentate phosphite ligand and a Group VIII metal. Besides the hydroformylation process described herein, this catalyst system can be used as a homogeneous catalyst for other reactions, including hydrocyanation, polymerization, hydroformylation, isomerization and carbonylation reactions. When the reaction is hydroformylation, the Group VIII metal is preferably rhodium, and a preferred catalyst system comprises a chelate complex of a bidentate phosphite ligand according to formula (1) and rhodium.

Rhodium can be used in the form of a rhodium compound which can include hydrides, halides, organic acid salts, inorganic acid salts, oxides, carbonyl compounds and amine compounds of these metals. Examples of useful rhodium compounds include $RhCl_3$, $Rh(NO_3)_3$, $Rh(OAc)_3$, $Rh_2O_3$, $Rh(acac)$ $(CO)_2$ $[Rh(OAc)$ $(COD)]_2$, $Rh_4(CO)_{12}$, $Rh_6(CO)_{16}$, $RhH(CO)$ $(Ph_3P)_3$, $[Rh(OAc)$ $(CO)_2]_2$ and $[RhCl(COD)]_2$ (wherein "acac" is an acetylacetonate group; "Ac" is an acetyl group; "COD" is 1,5-cyclooctadiene; and "Ph" is a phenyl group). However, as one skilled in this art will appreciate, other rhodium compounds can be used in the present invention, besides those specifically named herein.

Examples of other suitable Group VIII metals include cobalt, ruthenium, palladium, platinum, osmium and iridium. Examples of Group VIII metal compounds include ruthenium compounds (such as, for example, $Ru_3(CO)_{12}$, $Ru(NO_3)_3$, $RuCl_3(Ph_3P)_3$ and $Ru(acac)_3$), palladium compounds (such as, for example, $PdCl_2$, $Pd(OAc)_2$, $Pd(acac)_2$, $PdCl_2(COD)$ and $PdCl_2(Ph_3P)_2$), osmium compounds (such as, for example, $Os_3(CO)_{12}$ and $OsCl_3$), iridium compounds (such as, for example, $Ir_4(CO)_{12}$ and $IrSO_4$), platinum compounds (such as, for example, $K_2PtCl4$, $PtCl_2(PhCN)_2$ and $Na_2PtCl_6.6H_2O$), cobalt compounds (such as, for example, $CoCl_2$ $Co(NO_3)_2$, $Co(OAc)_2$ and $Co_2(CO)_8$), and rhodium compounds as described above.

The catalyst system can be prepared by mixing a suitable Group VIII metal compound with the bidentate phosphite ligand in a suitable solvent in accordance with known complex-forming methodology.

A further embodiment of the invention provides a class of new bidentate phosphite compounds according to any of formulas (1), (9), (10), (11) and (12), in which the structure of the bridging group $R^2$ is sufficiently flexible such that both phosphorous atoms of the ligand can coordinate with one rhodium atom, as described above. These new bidentate phosphite compounds can be prepared according to the processes described herein.

The operation of the hydroformylation process of the invention does not require a special molar ratio of bidentate phosphite ligand to Group VIII metal in the catalyst system. In other words, the bidentate phosphite ligand: Group VIII metal molar ratio is not critical to the practice of the invention, and one skilled in this art would know how to adjust the ratio to achieve the desired results. To achieve optimum catalyst activity and selectivity, the ratio of ligand to metal is preferably from about 1 to 100 (mol phosphite/ mol metal), and more preferably from 1 to 25 (mol phosphite/mol metal).

The amount of Group VIII metal present in the hydroformylation process is not critical to the practice of the invention. One skilled in this art would be able to select the appropriate metal and the appropriate amount to obtain favorable results and maximize catalyst activity and economy. In general, the amount of Group VIII metal used in the process and the catalyst system is between 10 ppm and 1000 ppm.

In the hydroformylation process of the invention the use of a solvent is not essential, although a solvent inert to the hydroformylation process may be used. For instance, the solvent may be the mixture of reactants of the hydroformylation itself, such as the starting unsaturated compound, the aldehyde product and/or by-products. Other suitable solvents include, for example, aromatic solvents (such as, for example, benzene, toluene, xylene, and dodecylbenzene), ketones (such as, for example, acetone, diethylketone and methylethylketone), ethers (such as, for example, tetrahydrofuran and dioxane), and esters (such as, for example, ethylacetate and di-n-octyl phthalate). A mixture of solvents may also be used.

The specific ethylenically unsaturated organic compound used in the hydroformylation process of the invention is not critical to the practice of the invention. The minimum criteria for the preparation of an aldehyde compound is that the ethylenically unsaturated organic compound has at least one ethylene (—HC═CH—) bond, for example —$CH_2$—HC═CH—$CH_2$—, —$CH_2$—HC═CH—$CH_3$, or —$CH_2$—HC═$CH_2$. The examples illustrate that the ethylene bond may be anywhere in the the molecule, or at the end of the molecule. Preferably, a $C_{2-20}$ ethylenically unsaturated organic compound is used.

Examples of useful ethylenically unsaturated organic compounds include linear terminal olefinic hydrocarbons (such as, for example, ethylene, propylene, 1-butene, 1,3-butadiene, 1-pentene, 1-hexene, 1-octene, 1-nonene, 1-decene, 1-tetradecene, 1-hexadecene, 1-octadecene, 1-eicosene and 1-dodecene; branched terminal olefinic hydrocarbons for example isobutene and 2-methyl-1-butene), linear internal olefinic hydrocarbons (such as, for example, cis- and trans-2-butene, cis- and - trans-2-hexene, cis- and - trans-3-hexene, cis- and trans-2-octene and cis- and trans-3-octene), branched internal olefinic hydrocarbons (such as, for example, 2,3-dimethyl-2-butene, 2-methyl-2-butene and 2-methyl-2-pentene), terminal olefinic hydrocarbon-internal olefinic hydrocarbon mixtures (such as, for example, octenes prepared by dimerization of butenes, olefin oligomer isomer mixtures of from dimer to tetramer of lower olefins including propylene, n-butene, isobutene or the like), and cycloaliphatic olefinic hydrocarbons (such as, for example, cyclopentene, cyclohexene, 1-methylcyclohexene, cyclooctene and limonene).

Examples of the olefinic compound carrying a hydrocarbon group substituent containing an unsaturated hydrocarbon group include olefinic compounds containing an aromatic substituent (such as, for example, styrene, α-methylstyrene and allylbenzene) and diene compounds (such as, for example, 1,5-hexadiene, 1,7-octadiene and norbornadiene).

The ethylenically unsaturated organic compound can carry as substituents one or more functional groups containing a heteroatom (such as, for example, oxygen, sulfur, nitrogen and phosphorous). Examples of these substituted olefinic compounds include vinyl methyl ether, methyl oleate, allyl alcohol, oleyl alcohol, 3-methyl-3-butene-1-ol, methyl 3-pentenoate, methyl 4-pentenoate, 3-pentenoic acid, 4-pentenoic acid, 3-hydroxy-1,7-octadiene, 1-hydroxy-2,7-octadiene, 1-methoxy-2,7-octadiene, 7-octene-1-al, hexa-1-en-4-ol, acrylonitrile, acrylic acid esters (such as, for example, methylacrylate), methacrylic acid esters (such as, for example, methylmethacrylate), vinyl acetate and 1-acetoxy-2,7-octadiene.

Preferred substrates include pentenenitrile, pentenoic acid and $C_1$–$C_6$ alkyl pentenoate ester compounds (such as, for example, 3-pentenenitrile, 3-pentenoic acid, methyl 3-pentenoate, ethyl 3-pentenoate and methyl 4-pentenoate). These compounds are preferred because the resulting aldehyde compounds can be advantageously used in the preparation of Nylon-6 and Nylon-6.6.

The specific reaction conditions necessary to conduct the hydroformylation process of the invention depend on the particular ethylenically unsaturated organic compound used as starting material. Generally, the temperature can be between room temperature up to 200° C., and preferably is from 50° to 150° C. The pressure is generally between normal atmospheric pressure to 20 MPa, and is preferably from 0.2 to 10 MPa and more preferably from 0.5 to 5 MPa. As a rule, the pressure is the combination of the partial pressures of hydrogen and carbon monoxide. However, inert gasses may also be present. The molar ratio of hydrogen: carbon monoxide is generally between 10:1 and 1:10, and is preferably between 2:1 and 1:2.

The hydroformylation process may be successfully run in various types of reaction systems. Examples of suitable reaction systems include continuous operations, semicontinuous operations and batch operations using, for example, a stirring tank reactor or a bubble tower tank reactor.

The present invention will be described in further detail in the following Examples. These Examples are for illustrative purposes only, and the invention is by no means restricted to the specific embodiments described in the Examples.

EXAMPLE I

Preparation of the Formula (9) Phosphite

The phosphite according to formula (9) was prepared by first preparing an aromatic molecule having four alcohol functional groups. This molecule was prepared by first reacting 3,4-dimethoxy acetophenone with 3,4-dimethoxybenzaldehyde according to the procedure described in Vogel "A text-book of practical organic chemistry", Longmans, 1966, page 718, for benzalacetophenone using 3,4-dimethoxyacetophenone instead of benzaldehyde.

The thus obtained 3,4-dimethoxybenzal 3,4-dimethoxyacetophenone was hydrogenated using Pd/silica gel in ethylacetate/ethanol (3:1) as described in J. Agric. Chem. Soc. Jpn. 27 (1953) 491. Subsequently, the carbonyl functional group was reduced by a Clemmensen cleavage. After reduction of the methoxy functional groups with HI the desired alcohol was obtained. The phosphite was prepared by reaction of 2-tert-butyl-4-methoxyphenyl phosphorous dichloride with the above prepared alcohol in toluene/dichloromethane. Purification was performed by column chromatography ($Al_2O_3$, $CH_2Cl_2$).

EXAMPLE II

Preparation of the Formula (10) Phosphite

The phosphite according to formula (10) was prepared by first preparing an aliphatic molecule having four alcohol functional groups, by reacting 1,6-dibromohexane with dimethylmalonate as described by G. R. Newkome et al in J. Am. Chem. Soc. 112 (1990) 8458. Subsequently, the ester groups in the resulting molecule were reduced with $LiAlH_4$ to obtain the alcohol. The phosphite was prepared as described in example I of U.S. Pat. No. 5,103,035 in which 2-tert-butyl-4-methoxyphenol instead of 2,4-di-tert-butylphenol and the above prepared alcohol was used. Purification was performed by column chromatography ($Al_2O_3$, $CH_2Cl_2$).

EXAMPLE III

Preparation of the Formula (11) Phosphite

The phosphite according to formula (11) was prepared using the method as described in Example I for the phosphite according to formula (9) using 2,4,6-tri-tert-butylphenyl phosphorous dichloride instead of 2-tert-butyl-4-methoxyphenyl phosphorous dichloride.

EXAMPLE IV

Preparation of the Formula (12) Phosphite

The phosphite according to formula (12) was prepared using the method as described in Example II for the phosphite according to formula (10) starting from 1,3-dibromopropane and dimethyl malonate.

EXAMPLE V

Hydroformylation of Methyl 3-pentenoate Using a Formula (9) Catalyst

A Hastelloy-C-steel autoclave having an internal volume of 150 ml was filled in an atmosphere of nitrogen with 5.8 mg ($2.25 \times 10^{-5}$ mol) Rh (acac) $(CO)_2$, $7.88 \times 10^{-5}$ mol phosphite according to formula (9) and 60 ml toluene. The autoclave was closed and flushed with nitrogen. During 1.5 hour the autoclave was heated to 90° C. and the pressure was increased to 1.0 MPa with a $H_2$/CO mixture (1:1 (mol:mol)). Subsequently a mixture of 5.1 g (45 mmol) methyl 3-pentenoate and 1 g nonane (gas chromatography internal standard) and an amount of toluene resulting in a 15 ml mixture was injected. The reaction mixture was analyzed with gas chromatography after 1.5 hour. The results are presented in Table 1.

EXAMPLE VI

Hydroformylation of Methyl 3-pentenoate Using a Formula (10) Catalyst

Example V was repeated with a phosphite according to formula 10. The amount of rhodium was the same as in Example V. See Table 1 for the bidentate phosphite/Rh ratio, reaction time and results.

EXAMPLE VII

Hydroformylation of Methyl 3-pentenoate Using a Formula (11) Catalyst

Example V was repeated with a phosphite according to formula (11). See Table 1 for results.

EXAMPLE VIIIa and VIIIb

Hydroformylation of Methyl 3-pentenoate Using a Formula (12) Catalyst

Example V was repeated with a phosphite according to formula (12). See Table 1 for results.

EXAMPLE IX

Hydroformylation of Methyl 3-pentenoate Using a Formula (3) Catalyst

Example V was repeated with phosphite according to formula (3). The results are presented in Table 1.

EXAMPLE X

Hydroformylation of Methyl 3-pentenoate Using a Formula (4) Catalyst

Example V was repeated with phosphite according to formula (4). The results are presented in Table 1.

COMPARATIVE EXAMPLE A

Hydroformylation of Methyl 3-pentenoate Using Formula 35 of EP-A-518,241

Example VIIIb was repeated with an equimolar amount of the following phosphite formula (13) (formula 35 of EP-A-518,241):

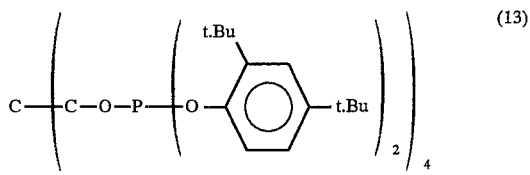

(13)

See Table 1 for results.

COMPARATIVE EXAMPLE B

Hydroformylation of Methyl 3-pentenoate Using Formula (14) in EP 518,241

Example VIII was repeated with an equimolar amount of the following bidentate phosphite formula (14):

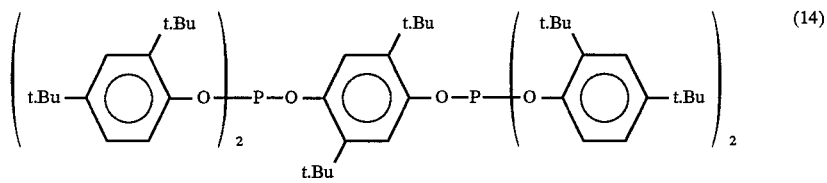

(14)

See Table 1 for results.

TABLE 1

| Example | phosphite (L) | L/Rh | time (hours) | conversion (%) | selectivity to aldehydes (%) | hydrogenation (%) |
|---|---|---|---|---|---|---|
| V | 9 (ex. I) | 3.5 | 1.5 | 27.4 | 82.7 | 17.3 |
| VI | 10 (ex. II) | 1.0 | 2.5 | 44.5 | 94.5 | 5.5 |
| VII | 11 (ex. III) | 7.8 | 24 | 10.7 | 83.9 | 16.1 |
| VIIIa | 12 (ex. IV) | 25 | 24 | 68.7 | 90.4 | 9.6 |
| VIIIb | 12 (ex. IV) | 5 | 25 | 98.3 | 87.0 | 13.0 |
| IX | 3 | 2 | 20.5 | 68.2 | 97.5 | 1 |
| X | 4 | 2 | 4 | 56.4 | 99.0 | 2.5 |
| A | 13 | 5 | 16 | 2.4 | 80.3 | 19.7 |
| B | 14 | 5 | 16 | 88.8 | 83.6 | 16.4 |

EXAMPLE XI

Hydroformylation of Trans-2-octene Using a Formula (9) Catalyst

Example V was repeated with the same amount of rhodium and a phosphite/bidentate phosphite ratio of 2. Instead of methyl 3-pentenoate, trans-2-octene was used as substrate. The results are presented in Table 2.

COMPARATIVE EXAMPLE C

Hydroformylation of Trans-2-octene Using Formula (14) in EP 518,241

Example XI was repeated with a phosphite according to formula (14). See Table 2 for results.

TABLE 2

| Example | phosphite (L) | time (hours) | conversion (%) | selectivity to aldehydes (%) | hydrogenation (%) |
|---|---|---|---|---|---|
| XI | 10 | 20 | 30.7 | 99.2 | 0.8 |
| C | 14 | 94 | 49.3 | 98.9 | 1.1 |

EXAMPLE XII

Hydroformylation of 1-octene Using a Formula (10) Catalyst

Example V was repeated in which a phosphite according to formula (10) with a L/Rh=2 and 1-octene as substrate is used. The results are presented in Table 3.

EXAMPLE XIII

Hydroformylation of 1-octene Using a Formula (3) Catalyst

Example XII was repeated using a phosphite according to formula (3). The results are presented in Table 3.

COMPARATIVE EXAMPLE D

Hydroformylation of 1-octene Using Formula (14) in EP 518,241

Example XII was repeated with a phosphite according to formula (14). The results are presented in Table 3.

TABLE 3

| Example | phosphite (L) | time (hours) | conversion (%) | selectivity to aldehydes (%) | hydrogenation (%) |
|---|---|---|---|---|---|
| XII | 10 | 3 | 93.0 | 99.7 | 0.3 |
| XIII | 3 | 3 | 80.6 | 98.9 | 1.1 |
| D | 14 | 3 | 57.9 | 97.7 | 2.3 |

The contents of all references mentioned above are incorporated herein in their entirety by reference.

We claim:

1. A process for preparing an aldehyde compound by hydroformylation of an ethylenically unsaturated organic compound in the presence of a Group VIII metal catalyst and a bidentate phosphite ligand having a chemical structure according to formula

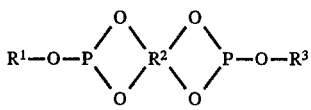

wherein $R^1$ and $R^3$ are organic groups which may be the same or different and which contain 1 to 30 carbon atoms selected from the group consisting of alkyl, cycloalkyl, aryl, aralkyl and alkaryl groups, and wherein $R^2$ is a tetravalent organic group having at least 4 and up to 35 carbon atoms.

2. The process according to claim 1, wherein $R^1$ and $R^3$ are selected from the group consisting of tert-butyl, isopropyl, cyclopentyl, cyclohexyl, phenyl, naphtyl, benzyl, phenethyl, mesityl, tolyl and xylyl groups.

3. The process according to claim 1, wherein $R^1$ and $R^3$ may be substituted with one or more $C_{1-12}$ organic group substituents selected from the group consisting of alkyl, aryl, alkoxy and trimethylsilyl groups.

4. The process according to claim 1, wherein $R^1$ and $R^3$ may be substituted with one or more halogen group substituents selected from the group consisting of fluoride, chloride and bromide groups.

5. The process according to claim 1, wherein $R^1$ and $R^3$ contain a heteroatom selected from the group consisting of N, S or Sn.

6. The process according to claim 1, wherein the structure of $R^2$ is flexible such that both phosphorous atoms of the bidentate phosphite ligand bond to one atom of the Group VIII metal catalyst.

7. The process according to claim 6, wherein $R^2$ comprises at least 8 carbon atoms.

8. The process according to claim 7, wherein $R^2$ is selected from the group consisting of an alkyltetraryl group, an orthoarylene-$(Q)_n$-orthoarylene group, an alkylene-$(Q)_n$-alkylene group or an orthoarylene-$(Q)_n$-alkylene group, wherein n is 0, 1, 2, 3 or 4 and Q is a divalent aryl group or alkyl group.

9. The process according to claim 8, wherein $R^2$ is an orthophenylene-$(Q)_n$-orthophenylene group, wherein Q is an —$(CR^4R^5)$— group in which $R^4$ and $R^5$ may be the same or different and are selected from the group consisting of hydrogen or a $C_{1-12}$ alkyl group.

10. The process according to claim 8, wherein $R^2$ is represented by the formula:

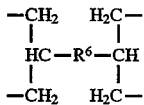

in which $R^6$ is an alkylene group having 2 to 7 carbon atoms.

11. The process according to claim 1, wherein the Group VIII metal catalyst is rhodium.

12. The process according to claim 1, wherein the ethylenically unsaturated organic compound is selected from the group consisting of pentenenitrile, pentenoic acid or a $C_1$-$C_6$ alkyl pentenoate ester.

* * * * *